(12) United States Patent
Schaning et al.

(10) Patent No.: US 11,832,879 B2
(45) Date of Patent: Dec. 5, 2023

(54) SYSTEMS AND METHODS FOR ENERGY DELIVERY

(71) Applicant: NeuWave Medical, Inc., Madison, WI (US)

(72) Inventors: Matthew Schaning, Madison, WI (US); Nicholas Katrana, Madison, WI (US); Matthew Thiel, Madison, WI (US); Louis Mingione, Madison, WI (US); Mark Thom, Madison, WI (US); Richard Schefelker, Madison, WI (US)

(73) Assignee: NeuWave Medical, Inc., Madison, WI (US)

( * ) Notice: Subject to any disclaimer, the term of this patent is extended or adjusted under 35 U.S.C. 154(b) by 1183 days.

(21) Appl. No.: 16/297,173

(22) Filed: Mar. 8, 2019

(65) Prior Publication Data
US 2020/0281652 A1    Sep. 10, 2020

(51) Int. Cl.
| A61B 18/18 | (2006.01) |
| A61B 18/00 | (2006.01) |
| A61L 29/06 | (2006.01) |
| A61L 29/14 | (2006.01) |
| A61M 25/01 | (2006.01) |

(52) U.S. Cl.
CPC ......... *A61B 18/1815* (2013.01); *A61L 29/06* (2013.01); *A61L 29/14* (2013.01); *A61B 2018/00023* (2013.01); *A61B 2018/00095* (2013.01); *A61B 2018/00273* (2013.01); *A61B 2018/00541* (2013.01); *A61B 2018/00577* (2013.01); *A61B 2018/00714* (2013.01); *A61B 2018/1861* (2013.01); *A61M 25/0133* (2013.01)

(58) Field of Classification Search
None
See application file for complete search history.

(56) References Cited

U.S. PATENT DOCUMENTS

| 3,800,552 A | 4/1974 | Sollami |
| 3,838,242 A | 9/1974 | Goucher |
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |

(Continued)

FOREIGN PATENT DOCUMENTS

| AU | 2015/202149 | 5/2015 |
| CN | 2579361 | 10/2003 |

(Continued)

OTHER PUBLICATIONS

Brace Christopher et al. "Analysis and experimental validation of a triaxial antenna for microwave tumor ablation" IEEE MTTS Int Microw Symp. Jun. 3, 2004(6-11) 1437-1440.

(Continued)

*Primary Examiner* — Joanne M Rodden
*Assistant Examiner* — Nora W Rhodes
(74) *Attorney, Agent, or Firm* — CASIMIR JONES, SC; Robert A. Goetz

(57) ABSTRACT

The present invention relates to flexible sheath assemblies capable of maintaining a desired positioning at a desired tissue region during medical procedures involving use insertion and withdrawal of medical tools through the flexible sheath, and related systems and methods.

13 Claims, 4 Drawing Sheets

(56) References Cited

U.S. PATENT DOCUMENTS

| | | |
|---|---|---|
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr |
| 4,586,491 A | 5/1986 | Carpenter |
| 4,589,424 A | 5/1986 | Vaguine |
| 4,601,296 A | 7/1986 | Yerushalmi et al. |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,800,899 A | 1/1989 | Elliott et al. |
| 4,815,450 A | 3/1989 | Patel |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner et al. |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Sterzer |
| 5,129,396 A | 7/1992 | Rosen |
| 5,150,717 A | 9/1992 | Rosen |
| 5,167,619 A | 12/1992 | Wuchinich |
| 5,211,625 A | 5/1993 | Sakurai |
| 5,213,561 A | 5/1993 | Weinstein et al. |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Milder |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,364,392 A | 11/1994 | Warner |
| 5,366,490 A | 11/1994 | Edwards |
| 5,369,251 A | 11/1994 | King |
| 5,370,678 A | 12/1994 | Edwards |
| 5,405,346 A | 4/1995 | Grundy |
| 5,431,649 A | 7/1995 | Mulier |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell |
| 5,559,295 A | 9/1996 | Sheryll |
| 5,575,794 A | 11/1996 | Walus |
| 5,578,029 A | 11/1996 | Trelles |
| 5,591,227 A | 1/1997 | Dinh |
| 5,597,146 A | 1/1997 | Putman |
| 5,599,295 A | 2/1997 | Rosen |
| 5,599,352 A | 2/1997 | Dinh |
| 5,603,697 A | 2/1997 | Grundy |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt |
| 5,921,935 A | 7/1999 | Hickey |
| 5,957,969 A | 9/1999 | Warner |
| 5,963,082 A | 10/1999 | Dick |
| 5,995,875 A | 11/1999 | Blewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |
| 6,165,163 A | 12/2000 | Chien |
| 6,174,307 B1 | 1/2001 | Daniel |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly |
| 6,223,085 B1 | 4/2001 | Dann |
| 6,230,060 B1 | 5/2001 | Mawhinney |
| 6,235,022 B1 | 5/2001 | Hallock |
| 6,241,725 B1 | 6/2001 | Cosman |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |
| 6,273,884 B1 | 8/2001 | Altshuler |
| 6,273,885 B1 | 8/2001 | Koop |
| 6,273,886 B1 | 8/2001 | Edwards |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,312,427 B1 | 11/2001 | Berube |
| 6,325,796 B1 | 12/2001 | Berube |
| 6,347,251 B1 | 2/2002 | Deng |
| 6,355,033 B1 | 3/2002 | Moorman |
| 6,364,876 B1 | 4/2002 | Erb |
| 6,383,182 B1 | 5/2002 | Berube |
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,351 B1 | 10/2002 | Woodruff |
| 6,461,352 B2 | 10/2002 | Morgan |
| 6,471,696 B1 | 10/2002 | Berube |
| 6,500,174 B1 | 12/2002 | Maguire |

(56) References Cited

U.S. PATENT DOCUMENTS

| | | |
|---|---|---|
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 | 6/2003 | Rittman, III et al. |
| 6,577,903 B1 | 6/2003 | Cronin |
| 6,582,426 B2 | 6/2003 | Moorman |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,673,068 B1 | 1/2004 | Berube |
| 6,683,625 B2 | 1/2004 | Muthusamy |
| 6,694,163 B1 | 2/2004 | Vining |
| 6,699,240 B2 | 3/2004 | Francischelli |
| 6,702,576 B2 | 3/2004 | Fischer |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire et al. |
| 6,878,147 B2 | 4/2005 | Prakash |
| 6,890,968 B2 | 5/2005 | Angeletakis |
| 6,893,436 B2 | 5/2005 | Woodard |
| 6,898,454 B2 | 5/2005 | Atalar |
| D507,649 S | 7/2005 | Padain |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | Van der Weide |
| 7,115,126 B2 | 10/2006 | Berube |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen |
| 7,266,407 B2 | 9/2007 | Li et al. |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 6/2008 | Van der Walt |
| 7,400,929 B2 | 7/2008 | Zelickson et al. |
| 7,402,140 B2 | 7/2008 | Spero |
| 7,410,484 B2 | 8/2008 | Littrup |
| 7,467,015 B2 | 12/2008 | Van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,035,570 B2 | 10/2011 | Prakash |
| 8,059,059 B2 | 11/2011 | Bonn |
| 8,093,500 B2 | 1/2012 | Deborski |
| 8,109,895 B2 | 2/2012 | Williams et al. |
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,357,148 B2 | 1/2013 | Boulais et al. |
| 8,403,924 B2 | 3/2013 | Behnke |
| 8,430,871 B2 | 4/2013 | Brannan |
| 8,454,589 B2 | 6/2013 | Deno |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |
| 10,058,312 B2 | 8/2018 | Lalonde |
| 2001/0020166 A1 | 9/2001 | Daly et al. |
| 2001/0039416 A1 | 11/2001 | Moorman et al. |
| 2001/0049524 A1 | 12/2001 | Morgan et al. |
| 2002/0022836 A1 | 2/2002 | Goble |
| 2002/0026187 A1 | 2/2002 | Swanson et al. |
| 2002/0026188 A1 | 2/2002 | Balbierz et al. |
| 2002/0040185 A1 | 4/2002 | Atalar et al. |
| 2002/0072742 A1 | 6/2002 | Schaefer |
| 2002/0087151 A1 | 7/2002 | Mody |
| 2002/0087157 A1 | 7/2002 | Sliwa et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash |
| 2003/0120268 A1 | 6/2003 | Bertolero |
| 2003/0130711 A1 | 7/2003 | Pearson et al. |
| 2004/0030367 A1 | 2/2004 | Yamaki et al. |

(56) References Cited

U.S. PATENT DOCUMENTS

| | | |
|---|---|---|
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 7/2004 | Sterzer |
| 2004/0158237 A1 | 8/2004 | Abboud |
| 2004/0186517 A1 | 9/2004 | Hill |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1 | 1/2005 | Turovskiy |
| 2005/0075629 A1 | 4/2005 | Chapelon |
| 2005/0107870 A1 | 5/2005 | Wang |
| 2005/0109900 A1 | 5/2005 | Schilt |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Weide |
| 2005/0245920 A1 | 11/2005 | Vitullo et al. |
| 2006/0064083 A1 | 3/2006 | Khalaj |
| 2006/0079886 A1 | 4/2006 | Orszulak et al. |
| 2006/0094956 A1 | 5/2006 | Rr Vismanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch |
| 2006/0276780 A1 | 12/2006 | Brace |
| 2006/0289528 A1 | 12/2006 | Chiu |
| 2007/0016180 A1 | 1/2007 | Lee |
| 2007/0021741 A1 | 1/2007 | Marwan et al. |
| 2007/0066972 A1 | 3/2007 | Ormsby |
| 2007/0185554 A1 | 8/2007 | Appling |
| 2007/0203551 A1 | 8/2007 | Cronin |
| 2007/0208389 A1 | 9/2007 | Amundson et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn et al. |
| 2009/0281536 A1 | 11/2009 | Beckman et al. |
| 2009/0306644 A1 | 12/2009 | Mayse et al. |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn et al. |
| 2011/0098696 A1 | 4/2011 | Brannan |
| 2011/0118723 A1 | 5/2011 | Turner |
| 2011/0118725 A1 | 5/2011 | Mayse |
| 2011/0213352 A1 | 9/2011 | Lee |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0035584 A1* | 2/2012 | Thompson-Nauman ................... A61M 25/04 604/506 |
| 2012/0053577 A1 | 3/2012 | Lee et al. |
| 2012/0059394 A1* | 3/2012 | Brenner .............. A61B 17/122 606/142 |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |
| 2012/0209257 A1 | 8/2012 | Weide et al. |
| 2012/0209261 A1 | 8/2012 | Mayse |
| 2012/0209296 A1 | 8/2012 | Mayse |
| 2012/0232544 A1 | 9/2012 | Willyard |
| 2012/0232549 A1 | 9/2012 | Willyard |
| 2012/0310228 A1 | 12/2012 | Bonn |
| 2012/0316551 A1 | 12/2012 | van der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham et al. |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1 | 10/2013 | Mallya et al. |
| 2013/0281851 A1 | 10/2013 | Carr |
| 2013/0306543 A1 | 11/2013 | Beisser |
| 2013/0338530 A1 | 12/2013 | Kassab |
| 2014/0005706 A1 | 1/2014 | Gelfand |
| 2014/0046174 A1 | 2/2014 | Ladtkow |
| 2014/0046176 A1 | 2/2014 | Ladtkow |
| 2014/0152656 A1 | 6/2014 | Yoo |
| 2014/0163664 A1 | 6/2014 | Goldsmith et al. |
| 2014/0276033 A1 | 9/2014 | Brannan |
| 2014/0276200 A1 | 9/2014 | Brannan |
| 2015/0148792 A1 | 5/2015 | Kim |
| 2015/0150628 A1 | 6/2015 | Buysse |
| 2015/0164587 A1 | 6/2015 | Bonn et al. |
| 2015/0190193 A1 | 7/2015 | Mayse |
| 2015/0250540 A1 | 9/2015 | Behdad |
| 2015/0342669 A1* | 12/2015 | Flanagan ........... A61B 18/1492 606/41 |
| 2015/0351839 A1 | 12/2015 | Brannan |
| 2015/0374438 A1 | 12/2015 | van der Weide |
| 2016/0331933 A1* | 11/2016 | Knutsen ........... A61M 25/0147 |
| 2019/0343581 A1* | 11/2019 | Panescu ................. A61B 34/20 |
| 2020/0113627 A1* | 4/2020 | Alas ...................... A61B 18/14 |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |

(56) References Cited

FOREIGN PATENT DOCUMENTS

| | | |
|---|---|---|
| CN | 101511295 | 8/2009 |
| CN | 101563042 | 10/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1723922 | 11/2006 |
| EP | 1723922 A | 11/2006 |
| EP | 2098184 | 9/2009 |
| EP | 2295000 | 3/2011 |
| EP | 2316370 | 5/2011 |
| EP | 1659969 | 10/2012 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| WO | WO 92/04934 | 4/1993 |
| WO | WO 93/09845 | 5/1993 |
| WO | WO 95/004385 | 9/1995 |
| WO | WO 97/48449 | 12/1997 |
| WO | WO 99/56643 | 11/1999 |
| WO | WO 00/57811 | 10/2000 |
| WO | WO 2000/057811 | 10/2000 |
| WO | WO 01/70114 | 9/2001 |
| WO | WO 03/039385 | 5/2003 |
| WO | WO 03/086498 | 10/2003 |
| WO | WO 03/088806 | 10/2003 |
| WO | WO 03/088858 | 10/2003 |
| WO | WO 2003/086190 | 10/2003 |
| WO | WO 2004/004586 | 1/2004 |
| WO | WO 04026122 | 1/2004 |
| WO | WO 04/033039 | 4/2004 |
| WO | WO 2004/084748 | 10/2004 |
| WO | WO 04/112628 | 12/2004 |
| WO | WO 2004/112628 | 12/2004 |
| WO | WO 2005/011049 | 2/2005 |
| WO | WO 05/034783 | 4/2005 |
| WO | WO 05/110265 | 11/2005 |
| WO | WO 06/002943 | 1/2006 |
| WO | WO 06/005579 | 1/2006 |
| WO | WO 06/008481 | 1/2006 |
| WO | WO 2006/002843 | 1/2006 |
| WO | WO 2006/004585 | 1/2006 |
| WO | WO 2006/084676 | 8/2006 |
| WO | WO 2006/12149 | 11/2006 |
| WO | WO 2006/122149 | 11/2006 |
| WO | WO 2006/127847 | 11/2006 |
| WO | WO 2007/076924 | 7/2007 |
| WO | WO 2007/112103 | 10/2007 |
| WO | WO 2008/008545 | 1/2008 |
| WO | WO 2008/044013 | 4/2008 |
| WO | WO 08/142686 | 11/2008 |
| WO | WO 2010/067360 | 6/2010 |
| WO | WO 11/008903 | 1/2011 |
| WO | WO 2011/017168 | 2/2011 |
| WO | WO 2011/140087 | 11/2011 |
| WO | WO-2012043034 A1 * | 4/2012 ......... A61B 1/00071 |
| WO | WO 2013/173481 | 11/2013 |

OTHER PUBLICATIONS

Brace Christopher et al. "Microwave Ablation with a Triaxial Antenna: Results in ex vivo Bovine Liver" IEEE Transations on Microwave Theory and Techniques vol. 53 No. 1 Jan. 2005.

English translation of a Decision of Refusal from related Japanese Patent Application No. 2013-509179 dated Jun. 30, 2015.

European Search Report dated Mar. 3, 2009 EP Patent Application No. 06 802 385.2.

Golio "The RF and microwave handbook" Edition: 2. Published by CRC Press 2001 ISBN 0849338592X 97808493859626.

Head Hayden W. et al. "Thermal Ablation for Hepatocellular Carcinoma" Gastroenterology 2004:127:S167-S178.

International Search Report PCT/US06/031644 dated Aug. 17, 2007.

International Search Report PCT/US06/032811 dated Jan. 25, 2007.

International Search Report PCT/US2005/014534 dated Nov. 29, 2005.

International Search Report PCT/US2006/017981 dated Sep. 7, 2006.

International Search Report PCT/US2006/028821 dated Mar. 21, 2007.

International Search Report PCT/US2006/033341 dated Aug. 17, 2007.

Seki Toshihito et al. "Ultrasonically Guided Percutaneous Microwave Coagulation Therapy for Small Hepatocellular Carcinoma" Cancer Aug. 1, 1994 vol. 74 No. 3 pp. 817-825.

European Search Report, EP Patent Application No. 11778168, dated Oct. 2, 2013.

International Preliminary Report, PCT/US2007/007464, dated Sep. 30, 2008.

International Preliminary Report on Patentability, PCT/US2012/071310, dated Aug. 19, 2014.

International Preliminary Report on Patentability, PCT/US2011/035000, dated Nov. 6, 2012.

International Preliminary Report on Patentability, PCT/US2010/043558, dated Jan. 31, 2012.

Guy, AW (1971) IEEE Trans. Microwave Theory Tech. 19 pp. 205-214.

European Search Report, EP Patent Application No. 128602497, dated Sep. 15, 2015.

European Search Report, EP Patent Application No. 108069295, dated Feb. 21, 2013.

European Search Report, EP Patent Application No. 07810483, dated Mar. 22, 2013.

International Search Report, PCT/US2007/016082, dated Jul. 21, 2008.

International Search Report, PCT/US2011/035000, dated Jan. 6, 2012.

International Search Report, PCT/US2012/071310, dated Feb. 25, 2013.

International Preliminary Report on Patentability, PCT/US2007/016082, dated Jan. 14, 2009.

"Carbon dioxide." Carbon dioxide—New World Encyclopedia. Web. <http://www.newworldencyclopedia.org/entry/Carbon_dioxide>.

International Patent Application No. PCT/US05/14534 dated Nov. 29, 2005.

International Search Report re: PCT/US16/58888 dated Feb. 15, 2017.

International Search Report re: PCT/US2016/058890 dated Jan. 19, 2017.

U.S. Appl. No. 09/847,181, filed May 1, 2001.
U.S. Appl. No. 10/370,179, filed Feb. 19, 2003.
U.S. Appl. No. 10/834,802, filed Apr. 29, 2004.
U.S. Appl. No. 10/961,761, filed Oct. 7, 2004.
U.S. Appl. No. 10/961,994, filed Oct. 7, 2004.
U.S. Appl. No. 10/980,699, filed Nov. 3, 2004.

(56) References Cited

OTHER PUBLICATIONS

U.S. Appl. No. 11/053,987, filed Feb. 8, 2005.
U.S. Appl. No. 11/236,985, filed Sep. 28, 2005.
U.S. Appl. No. 11/237,136, filed Sep. 28, 2005.
U.S. Appl. No. 11/237,430, filed Sep. 28, 2005.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
European Search Report, EP Patent Application No. 17168163.8, dated Sep. 13, 2017.
International Search Report & Written Opinion, International Patent Application No. PCT/US2017/027424, dated Oct. 9, 2017.
European Search Report dated Mar. 9, 2015, EP Patent Application No. 14189493.1.
Extended European Search Report, EP Patent Application No. 11778168 dated Sep. 24, 2013.
International Preliminary Report on Patentability re: PCT/US2007/007408 dated Sep. 30, 2008.
International Preliminary Report on Patentability re: PCT/US2016/058888 dated Dec. 11, 2017.
International Preliminary Report on Patentability re: PCT/US2016/058890 dated May 11, 2018.
International Search Report re: PCT/US2007/007408 dated Aug. 31, 2007.
Supplementary European Search Report dated May 20, 2019, EP Patent Application No. 168606976, 8 pages.
Ario Loeve et al.: "Scopes Too Flexible . . . and Too Stiff" IEEE Pulse, IEEE, USA, vol. 1, No. 3, Nov. 1, 2010, pp. 26-41.
International Search Report and Written Opinion, International Patent Application No. PCT/IB2020/051478, dated May 4, 2020, 16 pages.

* cited by examiner

SYSTEMS AND METHODS FOR ENERGY DELIVERY

FIELD OF INVENTION

The present invention relates to flexible sheath assemblies capable of maintaining a desired positioning at a desired tissue region during medical procedures involving use insertion and withdrawal of medical tools through the flexible sheath, and related systems and methods.

BACKGROUND

Endoscopic sheaths used as guides for tool placement need to be very flexible in order to navigate through peripheral locations that may include tortuous paths, especially in bronchoscopic cases. Once at a desired location, it is difficult for the end of the sheath to remain in place as tools (e.g., obturator, flexible ablation probe, other bronchoscopic tools, etc.) are swapped and/or repositioned. Patient movements due to breathing additionally contributes to movement of the sheath.

New flexible sheaths capable of maintaining a desired positioning through use of the flexible sheaths (e.g., during medical procedures involving use of medical tools inserted and withdrawn through the sheath) are needed.

The present invention addresses this need.

SUMMARY

The present invention relates to flexible sheath assemblies capable of maintaining a desired positioning at a desired tissue region during medical procedures involving use insertion and withdrawal of medical tools through the flexible sheath, and related systems and methods.

In certain embodiments, the present invention provides flexible sheaths for use in endoscopic procedures.

Such flexible sheaths are not limited to specific characteristics or designs.

In some embodiments, the flexible sheath comprises an elongate tubular body comprising a) an elongate tubular body proximal end having a proximal end opening and an elongate tubular body distal end having a distal end opening, and b) an elongate tubular body interior portion and an elongate tubular body exterior portion, wherein the elongate tubular body interior portion extends from the elongate tubular body proximal end to the elongate tubular body distal end, wherein the elongate tubular body exterior portion extends from the elongate tubular body proximal end to the elongate tubular body distal end; wherein the elongate tubular body interior portion comprises a hollow port extending into the proximal end opening, through the elongate tubular body proximal end, through the elongate tubular body distal end, and out the distal end opening, wherein the size of the hollow port is such that it can accommodate the passing of a properly sized tool into the hollow port, through the hollow port, and out the hollow port; wherein the diameter of the flexible sheath is less than 5 mm.

In some embodiments, the elongate tubular body interior portion further comprises an elongate tubular body coolant intake channel, an elongate tubular body distal end contained region, and an elongate tubular body coolant outtake channel, wherein the elongate tubular body distal end contained region is positioned at the elongate tubular body distal end, wherein the elongate tubular body interior portion is configured to a) receive coolant into the elongate tubular body proximal end via the elongate tubular body coolant intake channel, b) circulate the received coolant through the elongate tubular body coolant intake channel to the elongate tubular body distal end contained region, and c) circulate the coolant from the elongate tubular body distal end contained region through the elongate tubular body outtake channel and out of the elongate tubular body proximal end.

In some embodiments, the diameter of the elongate tubular body outtake channel is larger than the diameter of the elongate tubular body intake channel, or the diameter of the elongate tubular body outtake channel is smaller than the diameter of the elongate tubular body intake channel, or the diameter of the elongate tubular body outtake channel and the diameter of the elongate tubular body intake channel are identical.

In some embodiments, the hollow port, elongate tubular body intake channel, and elongate tubular body outtake channel are positioned in a multiaxial manner, or the hollow port, elongate tubular body intake channel, and elongate tubular body outtake channel are concentrically positioned in a coaxial manner.

In some embodiments, the coolant is selected from water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide, and a coolant gas compressed at or near its critical point.

In some embodiments, the distal end of the elongate tubular body exterior portion comprises one or more high thermal conductivity regions or one or more flexible-rigid regions.

In some embodiments, the one or more high thermal conductivity regions are configured to selectively attach with a tissue region upon contact with the tissue region such that the elongate tubular body distal end is stabilized in a desired position with respect to the tissue region; wherein upon attachment of the one or more high thermal conductivity regions with a tissue region, the one or more high thermal conductivity regions are configured to selectively detach from the tissue region such that the elongate tubular body distal end is destabilized from the desired position with respect to the tissue region.

In some embodiments, the one or more high thermal conductivity regions are configured to attain and maintain a temperature causing freezing of a tissue region to facilitate attachment of the tissue region to the high thermal conductivity region in order to stabilize the elongate tubular body distal end in a desired position with respect to the tissue region.

In some embodiments, temperature of the one or more high thermal conductivity regions is regulated through circulation of coolant into and out of the elongate tubular body containment region.

In some embodiments, the temperature of the one or more high thermal conductivity regions is regulated through circulation of coolant into and out of the elongate tubular body containment region via a Joule-Thompson effect, an endothermic chemical reaction, or an exothermic chemical reaction.

In some embodiments, the one or more high thermal conductivity regions comprise one or more of metal, plastic, ceramic, or mixture thereof.

In some embodiments, the one or more high thermal conductivity regions are flexible.

In some embodiments, the one or more flexible-rigid regions are configured to selectively alternate between a flexible state and a rigid state.

In some embodiments, if the one or more flexible-rigid regions are in a rigid state than the elongate tubular body distal end is stabilized in a desired position with respect to a tissue region in contact with the flexible-rigid region;

In some embodiments, if the one or more flexible-rigid regions are in a flexible state than the elongate tubular body distal end is not stabilized with respect to a tissue region in contact with the flexible-rigid region.

In some embodiments, the one or more flexible-rigid regions comprise thermoplastic polymers that have an appropriate glass-transition temperature of approximately 15-25 degrees Celsius.

In some embodiments, the thermoplastic polymer comprises copolymers of lactic acid and caprolactone.

In some embodiments, the thermoplastic polymer comprises a copolymer of L-lactide and caprolactone such as poly(L-lactide-co-caprolactone) with an L-lactide to caprolactone monomer ratio of 70:30 or less.

In some embodiments, the thermoplastic region is commercially available as PURASORB® PLC-7015 from Purac Biomaterials of Gorinchem, The Netherlands.

In some embodiments, the temperature of the one or more flexible-rigid regions is regulated through circulation of coolant into and out of the elongate tubular body containment region, wherein maintenance of a flexible-rigid region temperature at approximately −40 degrees Celsius results in a flexible state for the one or more flexible-rigid regions, wherein maintenance of a flexible-rigid region temperature at approximately −5 degrees Celsius results in a rigid state for the one or more flexible-rigid regions.

In some embodiments, the temperature of the one or more flexible-rigid regions is regulated through circulation of coolant into and out of the elongate tubular body containment region via a Joule-Thompson effect, an endothermic chemical reaction, or an exothermic chemical reaction.

In some embodiments, the properly sized tool is selected from an obturator, ablation probe, energy delivery device, biopsy tool, etc.

In some embodiments, the flexible sheath has sufficient flexibility to access a circuitous route through a subject (e.g., through a branched structure, through a bronchial tree, through any region of the body to reach a desired location).

In some embodiments, the composition of the elongate tubular body is a polymer material.

In some embodiments, the composition of the elongate tubular body is a higher temperature rated polymer material.

In some embodiments, the composition of the elongate tubular body is fluorinated ethylene propylene (FEP) or a thermoplastic copolyester (e.g., Arnitel).

In some embodiments, the composition of the elongate tubular body is a fluoropolymer. In some embodiments, the fluoropolymer is perfluoromethylalkoxy alkane (MFA) or perfluoroalkoxy alkane (PFA).

In some embodiments, the elongate tubular body interior region further comprises a steerable pull ring configured to permit a user to steer the flexible sheath in any desired manner.

In some embodiments, the flexible sheath is designed to be operational within a microwave field or microwave zone (e.g., the flexible sheaths are microwave compatible) without sustaining microwave field or microwave zone related damage.

In some embodiments, the flexible sheath is designed to be operational within a tissue region experiencing high temperatures (e.g., the flexible sheaths are thermal resistant) without sustaining high temperature related damage.

In certain embodiments, the present invention provides systems comprising a primary catheter, a flexible sheath as described above, and an energy delivery device. In some embodiments, the primary catheter is an endoscope. In some embodiments, the energy delivery device is a microwave energy delivery device.

In certain embodiments, the present invention provides methods of treating a tissue region, comprising providing a system as described above, inserting the primary catheter into a tissue region, inserting the flexible sheath through the primary catheter to a desired tissue region to be treated, securing the flexible sheath at the desired tissue region to be treated via either the one or more high thermal conductivity regions or the one or more flexible-rigid regions, inserting the energy delivery device through the flexible sheath to the desired tissue region to be treated, and treating the tissue region to be treated with the energy delivery device. In some embodiments, the tissue region to be treated is within a subject. In some embodiments, the subject is a human subject.

Additional embodiments are described herein.

DETAILED DESCRIPTION

Figure 1:
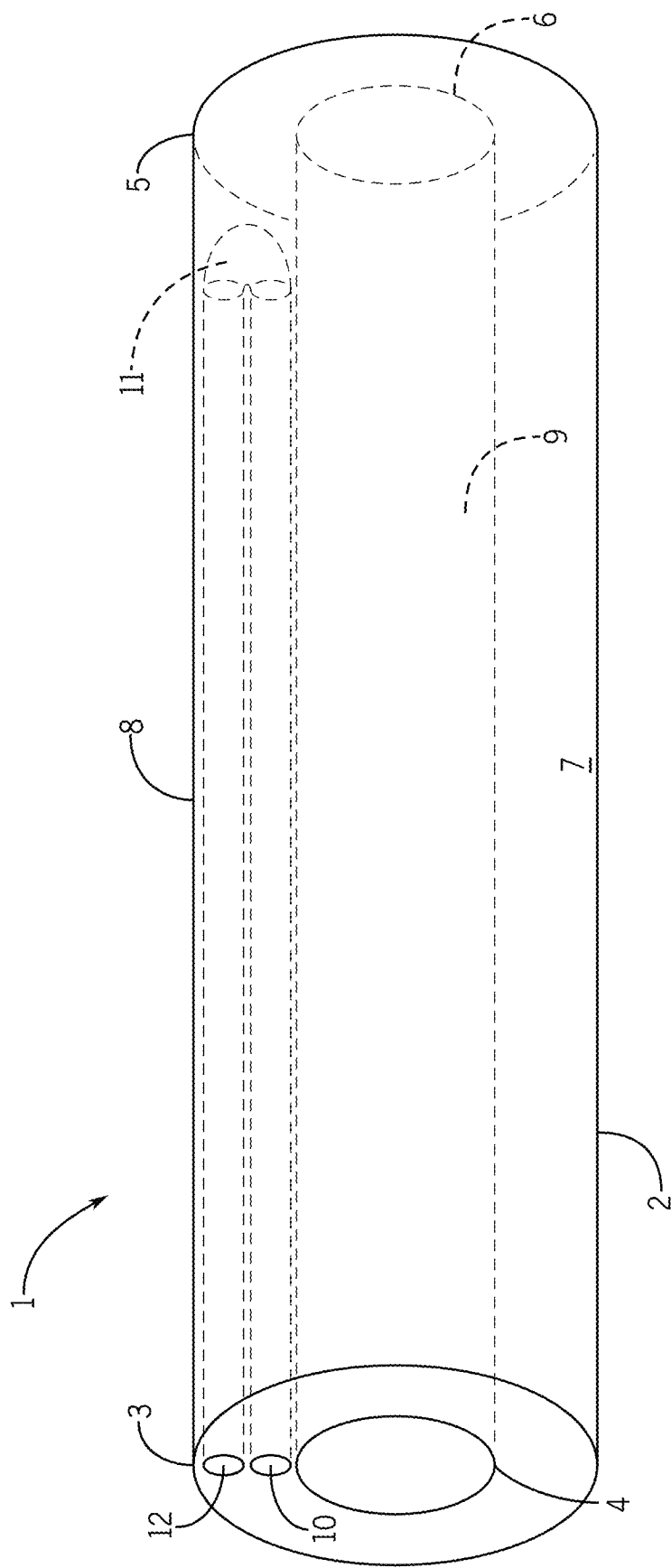
FIGS. 1-4 show various flexible sheath embodiments.

Therapeutic endoscopy or interventional endoscopy pertains to an endoscopic procedure during which a treatment (e.g., tissue ablation) (e.g., tissue collection) is carried out via the endoscope. This contrasts with diagnostic endoscopy, where the aim of the procedure is purely to visualize an internal part of a body (e.g., gastrointestinal region, respiratory region, urinary tract region, etc.) in order to aid diagnosis. In practice, a procedure which starts as a diagnostic endoscopy may become a therapeutic endoscopy depending on the findings.

Generally, therapeutic endoscopy involves the administration of an endoscope ("primary catheter") into a body region until a natural stopping positioning is reached (e.g., until the circumference of the body region inhibits further advancement of the endoscope). Next, a flexible sheath having a circumference smaller than the circumference of the endoscope is advanced through the endoscope and to a desired body region location. Next, a therapeutic tool (e.g., an ablation energy delivery tool) (e.g., a tissue collection tool) having a circumference smaller than the diameter of the flexible sheath is advanced through the flexible sheath to the desired body region location. Next, ablation energy is delivered to the desired body region location. Upon completion of the therapeutic endoscopy, the ablation energy delivery tool is withdrawn through the flexible sheath, the flexible sheath is withdrawn through the endoscope, and the endoscope is withdrawn from the subject.

Such flexible sheaths used as guides for tool placement need to be very flexible in order to navigate through peripheral locations that may include tortuous paths, especially in bronchoscopic cases. Once at a desired location, it is difficult for the end of the flexible sheath to remain in place as tools (e.g., obturator, flexible ablation probe, other bronchoscopic tools, etc.) are swapped and/or repositioned and natural patient movement (e.g., breathing) contributes to undesired movement of the flexible sheath from the desired tissue region (e.g., the tissue region where a medical procedure is occurring).

Accordingly, new flexible sheaths capable of maintaining a desired positioning at a desired tissue region during medical procedures involving use insertion and withdrawal of medical tools are needed.

The present invention addresses this need through providing flexible sheaths capable of maintaining a desired positioning at a desired tissue region during medical procedures involving use insertion and withdrawal of medical tools and through patient body movement. Such flexible sheath assemblies are configured for use in any kind of endoscopic energy delivery procedure (e.g., tissue ablation, resection, cautery, vascular thrombosis, treatment of cardiac arrhythmias and dysrhythmias, electrosurgery, tissue harvest, etc.).

Accordingly, the present invention relates to flexible sheath assemblies capable of maintaining a desired positioning at a desired tissue region during medical procedures involving use insertion and withdrawal of medical tools through the flexible sheath, and related systems and methods.

The flexible sheaths of the present invention are not limited to particular size dimensions. Indeed, in some embodiments, the size dimension of the flexible sheath is such that it is able to fit within and pass through the lumen of a primary catheter (e.g., an endoscope). In some embodiments, the flexible sheath is of sufficient diameter (e.g. 1 mm . . . 2 mm . . . 3 mm . . . 4 mm . . . 5 mm) to accommodate within and through its interior one or more suitable tools (e.g., energy delivery device, steerable navigation catheter). In some embodiments, the flexible sheath is of sufficient length to extend from an insertion site (e.g. mouth, incision into body of subject, etc.) to a desired target region within a living body (e.g. 50 cm . . . 75 cm . . . 1 m . . . 1.5 m . . . 2 m . . . 10 m . . . 25 m, etc.). In some embodiments, the flexible sheath is of sufficient length to extend through and beyond the reach of a primary catheter (e.g., endoscope) to reach a treatment site (e.g. peripheral lung tissue, heart tissue, gastrointestinal tissue, etc.) (e.g., any desired location within a living body).

The flexible sheaths of the present invention are not limited to a particular manner of navigation through a primary catheter and/or through a body region. In some embodiments, the flexible sheath comprises a navigation and/or steering mechanism. In some embodiments, the flexible sheath is without an independent means of navigation, position recognition, or maneuvering. In some embodiments, the flexible sheath relies upon the primary catheter (e.g., endoscope) or a steerable navigation catheter for placement.

FIG. 1 shows a flexible sheath 1 embodiment of the present invention. The flexible sheath 1 is not limited to a particular design or configuration. In some embodiments, the design or configuration of the flexible sheath 1 is such that it is able to be positioned at a desired tissue region and maintain that desired positioning during medical procedures involving use insertion and withdrawal of medical tools through the flexible sheath. In some embodiments, the flexible sheath 1 has sufficient flexibility to access a circuitous route through a subject (e.g., through a branched structure, through a bronchial tree, through any region of the body to reach a desired location).

In certain embodiments, as shown in FIG. 1, the flexible sheath 1 has an elongate tubular body 2 comprising an elongate tubular body proximal end 3 having a proximal end opening 4, an elongate tubular body distal end 5 having a distal end opening 6, an elongate tubular body interior portion 7 extending from the elongate tubular body proximal end 3 to the elongate tubular body distal end 5, and an elongate tubular body exterior portion 8 extending from the elongate tubular body proximal end 3 to the elongate tubular body distal end 5. In some embodiments, the arrangement and positioning of the elongate tubular body proximal end 3, proximal end opening 4, elongate tubular body distal end 5, distal end opening 6, elongate tubular body interior portion 7, and elongate tubular body exterior portion 8 within the elongate tubular body 2 is not limited. In some embodiments, the arrangement and positioning of the elongate tubular body proximal end 3, proximal end opening 4, elongate tubular body distal end 5, distal end opening 6, elongate tubular body interior portion 7, and elongate tubular body exterior portion 8 within the elongate tubular body 2 is such that it renders the flexible sheath 1 capable of being positioned at a desired tissue region and maintaining that desired positioning during medical procedures involving use insertion and withdrawal of medical tools through the flexible sheath 1.

Still referring to FIG. 1, the elongate tubular body 2 is not limited to a particular composition. In some embodiments, the composition of the elongate tubular body 2 is any composition that renders the flexible sheath 1 capable of being positioned at a desired tissue region and maintaining that desired positioning during medical procedures involving use insertion and withdrawal of medical tools through the flexible sheath 1. In some embodiments, the composition of the elongate tubular body 2 is a polymer material. In some embodiments, the composition of the elongate tubular body 2 is a higher temperature rated polymer material. Such embodiments are not limited to a particular higher temperature rated polymer material. In some embodiments, the higher temperature rated polymer material is fluorinated ethylene propylene (FEP). In some embodiments, the higher temperature rated polymer material is a thermoplastic copolyester. In some embodiments, the thermoplastic copolyester is Arnitel. In some embodiments, the higher temperature rated polymer material is a fluoropolymer. Such embodiments are not limited to a particular fluoropolymer. In some embodiments, the fluoropolymer is perfluoromethylalkoxy alkane (MFA). In some embodiments, the fluoropolymer is perfluoroalkoxy alkane (PFA). In some embodiments, only a portion (5%, 10%, 25%, 50%, 75%, 77%, 79%, 85%, 88%, 90%, 94%, 98%, 99%, 99.999%) of the elongate tubular body 2 has a composition of a higher temperature rated polymer material. In some embodiments, only a portion (5%, 10%, 25%, 50%, 75%, 77%, 79%, 85%, 88%, 90%, 94%, 98%, 99%, 99.999%) starting from the elongate tubular body distal end 5 has a composition of a higher temperature rated polymer material. In some embodiments, the entire elongate tubular body 2 has a composition of a higher temperature rated polymer material.

Still referring to FIG. 1, the flexible sheath 1 is configured such that devices (e.g., medical devices) can be inserted and withdrawn through the elongate tubular body interior portion 7. Examples of such devices that can be inserted and withdrawn through the elongate tubular body interior portion 7 include, but are not limited to, an obturator, ablation probe, energy delivery device, biopsy tool, etc.

Still referring to FIG. 1, the elongate tubular body interior portion 7 is not limited to particular configuration permitting the insertion and withdrawal of devices. In some embodiments, the elongate tubular body interior portion 7 has therein a hollow port 9 extending from the proximal end opening 4, through the elongate tubular body proximal end 3, through the elongate tubular body distal end 5, and out the distal end opening 6. The hollow port 9 is not limited to a particular size. In some embodiments, the size of the hollow port 9 is such that it can accommodate the insertion and withdrawal of a properly sized device (e.g., a device having a circumference smaller than the circumference of the hollow port 9) through its entirety. In some embodiments, the size of the hollow port 9 is such that it can accommodate the insertion and withdrawal of a properly sized device (e.g., a device having a circumference smaller than the circumference of the hollow port 9) through its entirety without compromising the ability of the flexible sheath 1 to be positioned at a desired tissue region and maintaining that desired positioning during medical procedures.

Still referring to FIG. 1, the elongate tubular body interior portion 7 is configured to circulate a coolant for purposes of maintaining the distal end of the elongate tubular body distal end 5 at a desired temperature. The elongate tubular body interior portion 7 is not limited to a particular manner of circulating a coolant for purposes of maintaining the distal end of the elongate tubular body distal end 5 at a desired temperature. In some embodiments, as shown in FIG. 1, the elongate tubular body interior portion 7 is able to circulate a coolant for purposes of maintaining the distal end of the elongate tubular body distal end 5 at a desired temperature through use of an elongate tubular body coolant intake channel 10, an elongate tubular body distal end contained region 11 positioned at the elongate tubular body distal end 5, and an elongate tubular body coolant outtake channel 12. Indeed, in some embodiments, the elongate tubular body interior portion 7 is configured to a) receive coolant into the elongate tubular body proximal end 3 via the elongate tubular body coolant intake channel 10, b) circulate the received coolant through the elongate tubular body coolant intake channel 10 to the elongate tubular body distal end contained region 11, and c) circulate the coolant from the elongate tubular body distal end contained region 11 through the elongate tubular body outtake channel 12 and out of the elongate tubular body proximal end 3.

Figure 2:
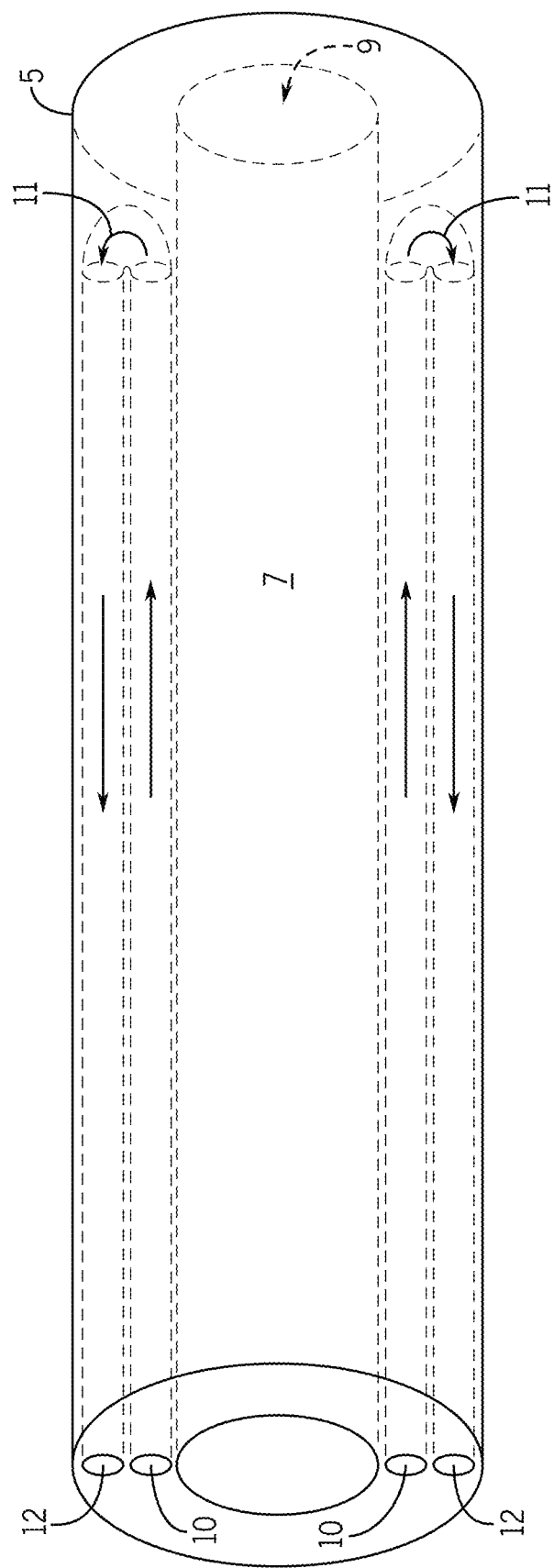

The hollow tube 9, elongate tubular body coolant intake channel 10, elongate tubular body distal end contained region 11, and elongate tubular body coolant outtake channel 12 are not limited to a particular positioning within the elongate tubular body interior portion 7. In some embodiments, as shown in FIG. 1, the hollow tube 9, elongate tubular body coolant intake channel 10, elongate tubular body distal end contained region 11, and elongate tubular body coolant outtake channel 12 are positioned in a multi-axial relationship. In some embodiments, as shown in FIG. 2, the hollow tube 9, elongate tubular body coolant intake channel 10, elongate tubular body distal end contained region 11, and elongate tubular body coolant outtake channel 12 are positioned in a concentric relationship with, for example, the hollow tube 9 surrounded by the elongate tubular body coolant outtake channel 12 which is surrounded by the elongate tubular body coolant intake channel 10, and the elongate tubular body distal end contained region 11 positioned at the distal end of the elongate tubular body exterior 8.

The elongate tubular body coolant intake channel 10 and elongate tubular body coolant outtake channel 12 are not limited to particular sizes. In some embodiments, the diameter of the elongate tubular body outtake channel 12 is larger than the diameter of the elongate tubular body intake channel 10. In some embodiments, the diameter of the elongate tubular body outtake channel 12 is smaller than the diameter of the elongate tubular body intake channel 10. In some embodiments, the diameter of the elongate tubular body outtake channel 12 and the diameter of the elongate tubular body intake channel are identical 10.

The elongate tubular body distal end contained region 11 is not limited to a particular size. In some embodiments, the size of the elongate tubular body distal end contained region 11 is such that it is able to accommodate coolant circulated through the elongate tubular body coolant intake channel 10 for purposes of maintaining the distal end of the elongate tubular body distal end 5 at a desired temperature (described in more detail below).

Such embodiments are not limited to use of a specific type or kind of coolant. In some embodiments, the coolant is selected from water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide, and a coolant gas compressed at or near its critical point.

Figure 3:
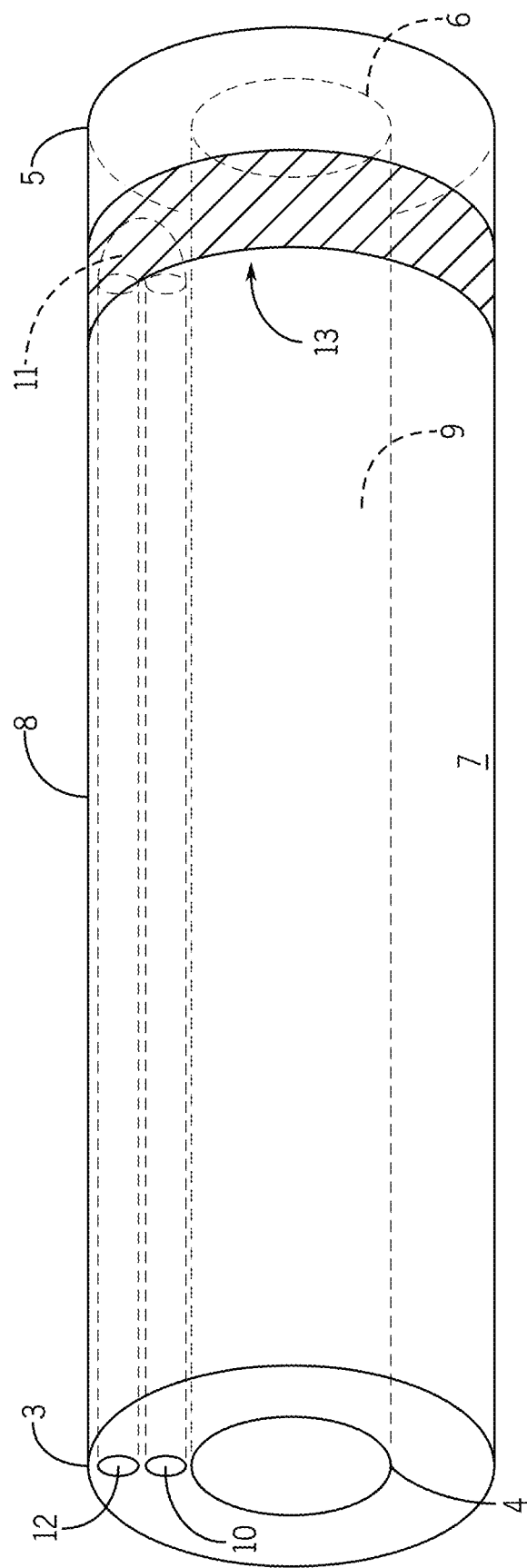

FIG. 3 shows a flexible sheath 1 wherein the distal end of the elongate tubular body exterior portion 5 comprises one or more high thermal conductivity regions 13 (as shown in FIG. 3 there is one high thermal conductivity region 13). In some embodiments, the high thermal conductivity region 13 is configured to selectively attach with a tissue region upon contact with the tissue region such that the elongate tubular body distal end 5 is stabilized in a desired position with respect to the tissue region.

The high thermal conductivity region 13 is not limited to a particular positioning along the distal end of the elongate tubular body exterior portion 8. In some embodiments, as shown in FIG. 3, the high thermal conductivity region 13 wraps around a portion (e.g., 1%, 5%, 10%, 25%, 45%, 49.9%, 50%, 55%, 62%, 70%, 79.5%, 85%, 90%, 92%, 93.5%, 98%, 99%, 99.99%) of the distal end of the elongate tubular body exterior portion 8. In some embodiments, the high thermal conductivity region 13 covers only a portion (e.g., 1%, 5%, 10%, 25%, 45%, 49.9%, 50%, 55%, 62%, 70%, 79.5%, 85%, 90%, 92%, 93.5%, 98%, 99%, 99.99%) of the of the distal end of the elongate tubular body exterior portion 8 but does not wrap around the entirety of the distal end of the elongate tubular body exterior portion 8.

The flexible sheath is not limited to a particular number of high thermal conductivity regions 13. In some embodiments, there is one high thermal conductivity region 13, as shown in FIG. 3. In some embodiments, there are 2, 3, 5, 8, 10, 25, 100, 1000, etc. high thermal conductivity regions 13 positioned along the distal end of the elongate tubular body exterior portion 8.

The high thermal conductivity region 13 is not limited to a particular manner of selectively attaching with a tissue region upon contact with the tissue region such that the elongate tubular body distal end 5 is stabilized in a desired position with respect to the tissue region. In some embodiments, the high thermal conductivity region 13 is able to selectively attach with a tissue region upon contact with the tissue region such that the elongate tubular body distal end 5 is stabilized in a desired position with respect to the tissue region through selective temperature adjustment of the high thermal conductivity region 13. For example, in some embodiments, upon positioning of the flexible sheath 1 to a desired location, selective reduction of the high thermal conductivity region 13 permits the tissue region to freeze onto the high thermal conductivity region 13 thereby securing the elongate tubular body distal end 5 to that desired location. In some embodiments, selective reduction of the high thermal conductivity region 13 permits the tissue region to freeze onto the high thermal conductivity region 13 thereby securing the elongate tubular body distal end 5 to that desired location during insertion and withdrawal of the devices through the hollow port 9. In some embodiments wherein the high thermal conductivity region 13 is secured with a tissue region, selectively increasing the temperature of the high thermal conductivity region 13 results in detachment (e.g., un-freezing) of the tissue region from the high thermal conductivity region 13.

The flexible sheath 1 is not limited to particular manner of selectively maintaining the temperature of the high thermal conductivity region 13. In some embodiments, the temperature of the high thermal conductivity region 13 is maintained and/or adjusted through circulation coolant into and out of the elongate tubular body distal end contained region 11. Indeed, the positioning of the high thermal conductivity region 13 is such that coolant circulated into the elongate tubular body distal end contained region 11 results in temperature adjustment/maintenance for the high thermal conductivity region 13. For example, in some embodiments, upon positioning of the flexible sheath 1 at a desired tissue location, coolant is circulated into the elongate tubular body distal end contained region 11 such that the temperature of the high thermal conductivity region 13 is lowered to a level wherein the tissue region attaches (e.g., freezes) onto the high thermal conductivity region. For example, maintaining tissue region attachment with the high thermal conductivity region 13 is accomplished through maintaining sufficient circulation of coolant into the elongate tubular body distal end contained region 11 to retain the high thermal conductivity region 13 at a temperature permitting such attachment. For example, increasing the temperature of the high thermal conductivity region 13 through reducing circulation of coolant into the elongate tubular body distal end contained region 11 facilitates detachment of the tissue region from the high thermal conductivity region 13. For example, increasing the temperature of the high thermal conductivity region 13 through increasing circulation of a higher temperature coolant into the elongate tubular body distal end contained region 11 facilitates detachment of the tissue region from the high thermal conductivity region 13.

In some embodiments, the temperature of the high thermal conductivity region 13 is regulated through circulation of coolant into and out of the elongate tubular body containment region 11 via a Joule-Thompson effect, an endothermic chemical reaction, or an exothermic chemical reaction.

In some embodiments, the material of the high thermal conductivity region 13 comprises one or more of metal, plastic, ceramic, or mixture thereof. In some embodiments, the material of the high thermal conductivity region 13 is flexible (e.g., as flexible as the remainder of the flexible sheath 1).

Figure 4:
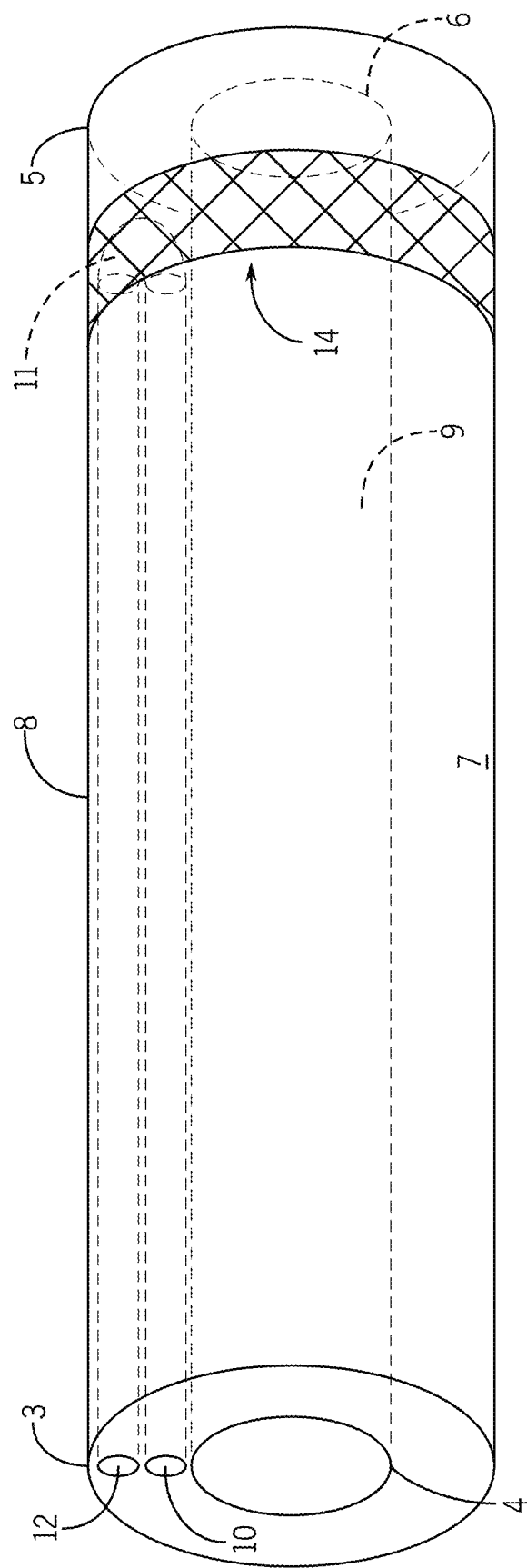

FIG. 4 shows a flexible sheath 1 wherein the distal end of the elongate tubular body exterior portion 5 comprises a flexible-rigid region 14. In some embodiments, the flexible-rigid region 14 is configured to selectively alternate between a flexible state and a rigid state. In some embodiments, the flexible-rigid region 14 is configured to selectively alternate between a flexible state and a rigid state for purposes of stabilizing the elongate tubular body distal end 5 with respect to a tissue region in contact with the flexible-rigid region 14.

The flexible-rigid region 14 is not limited to a particular positioning along the distal end of the elongate tubular body exterior portion 8. In some embodiments, as shown in FIG. 4, the flexible-rigid region 14 wraps around a portion (e.g., 1%, 5%, 10%, 25%, 45%, 49.9%, 50%, 55%, 62%, 70%, 79.5%, 85%, 90%, 92%, 93.5%, 98%, 99%, 99.99%) of the distal end of the elongate tubular body exterior portion 8. In some embodiments, the flexible-rigid region 14 covers only a portion (e.g., 1%, 5%, 10%, 25%, 45%, 49.9%, 50%, 55%, 62%, 70%, 79.5%, 85%, 90%, 92%, 93.5%, 98%, 99%, 99.99%) of the of the distal end of the elongate tubular body exterior portion 8 but does not wrap around the entirety of the distal end of the elongate tubular body exterior portion 8.

The flexible-rigid region 14 is not limited to a particular manner of selectively stabilizing the elongate tubular body distal end 5 with respect to a tissue region in contact with the flexible-rigid region 14. In some embodiments, flexible-rigid region 14 is able to selectively stabilize the elongate tubular body distal end 5 with respect to a tissue region in contact with the flexible-rigid region 14 through selective temperature adjustment of the flexible-rigid region 14. For example, in some embodiments, upon positioning of the flexible sheath 1 to a desired location, selectively increasing the temperature of the flexible-rigid region 14 renders the flexible-rigid region 14 into a rigid state which facilitates an anchoring of the elongate tubular body distal end 5 at the desired location. For example, in some embodiments, upon positioning of the flexible sheath 1 to a desired location, selectively increasing the temperature of the flexible-rigid region 14 renders the flexible-rigid region 14 into a rigid state which facilitates an anchoring of the elongate tubular body distal end 5 at the desired location during insertion and withdrawal of the devices through the hollow port 9. In some embodiments wherein the flexible-rigid region 14 is anchored at a tissue region (e.g., the flexible-rigid region 14 is in a rigid state), selectively decreasing the temperature of the flexible-rigid region 14 results in transition of the flexible-rigid region 14 to a flexible state which thereby releases the elongate tubular body distal end 5 from an anchoring with the tissue region.

The flexible sheath 1 is not limited to particular manner of selectively maintaining the temperature of the flexible-rigid region 14 for purposes of alternating between a flexible or rigid state. In some embodiments, the temperature of the flexible-rigid region 14 is maintained and/or adjusted through circulation coolant into and out of the elongate tubular body distal end contained region 11. Indeed, the positioning of the flexible-rigid region 14 is such that coolant circulated into the elongate tubular body distal end contained region 11 results in temperature adjustment/maintenance for the flexible-rigid region 14. For example, in some embodiments, upon positioning of the flexible sheath 1 at a desired tissue location, coolant is circulated into the elongate tubular body distal end contained region 11 such that the temperature of the flexible-rigid region 14 is either increased or decreased or maintained to achieve a desired rigidity or flexibility for the flexible-rigid region 14 thereby achieving either an anchoring with a tissue region or de-anchoring with the tissue region.

In some embodiments, the flexible-rigid region 14 comprises thermoplastic polymers that have an appropriate glass-transition temperature of approximately 15-25 degrees Celsius. In some embodiments, the thermoplastic polymer comprises copolymers of lactic acid and caprolactone. In some embodiments, the thermoplastic polymer comprises a copolymer of L-lactide and caprolactone such as poly(L- lactide-co-caprolactone) with an L-lactide to caprolactone monomer ratio of 70:30 or less. In some embodiments, the thermoplastic region is commercially available as PURASORB® PLC-7015 from Purac Biomaterials of Gorinchem, The Netherlands.

In some embodiments, the temperature of the flexible-rigid region 14 is regulated through circulation of coolant into and out of the elongate tubular body containment region 11 via a Joule-Thompson effect, an endothermic chemical reaction, or an exothermic chemical reaction.

In some embodiments, the flexible sheaths further contain a steerable pull ring. Such embodiments are not limited to a particular configuration for the steerable pull ring. In some embodiments, the steerable pull ring has any configuration that permits a user to manually steer the flexible sheath via manipulation of the steerable pull ring (e.g., manipulation of one or both of the wires results in a curving or steering of the sheath).

In some embodiments, the steerable pull ring permits the flexible sheath to be steered in any desired manner or direction. For example, in some embodiments, the steerable pull ring permits the flexible sheath to be steered at any desired curve angle (e.g., from 1 to 180 degrees). In some embodiments, the steerable pull ring permits the flexible sheath to be steered at any desired bend angle (e.g., from 1 to 360 degrees). In some embodiments, the steerable pull ring permits the flexible sheath to be steered at any desired bend radius (e.g., from 1 to 360 degrees). In some embodiments, the steerable pull ring permits the flexible sheath to be steered at any desired curve diameter. In some embodiments, the steerable pull ring permits the flexible sheath to be steered at any desired reach (e.g., from 0.1 to 100 mm). In some embodiments, the steerable pull ring permits the flexible sheath to be steered at any desired curl. In some embodiments, the steerable pull ring permits the flexible sheath to be steered at any desired sweep. In some embodiments, the steerable pull ring permits the flexible sheath to be steered at any desired curve (e.g., symmetrical or asymmetrical) (e.g., multi-curve or compound curve). In some embodiments, the steerable pull ring permits the flexible sheath to be steered at any desired loop. In some embodiments, the steerable pull ring permits the flexible sheath to be steered at any desired deflection (e.g., on-plane deflection, off plane deflection).

In some embodiments, the present invention provides systems for therapeutic endoscopic procedures wherein flexible sheaths as described herein, primary catheters, and one or more suitable tools (e.g., energy delivery device, steerable navigation catheter) are provided.

Such embodiments are not limited to a particular type or kind of primary catheter. In some embodiments, the present invention primary catheter is an endoscope. In some embodiments, any suitable endoscope known to those in the art finds use as a primary catheter in the present invention. In some embodiments, a primary catheter adopts characteristics of one or more endoscopes and/or bronchoscopes known in the art, as well as characteristics described herein. One type of conventional flexible bronchoscope is described in U.S. Pat. No. 4,880,015, herein incorporated by reference in its entirety. The bronchoscope measures 790 mm in length and has two main parts, a working head and an insertion tube. The working head contains an eyepiece; an ocular lens with a diopter adjusting ring; attachments for suction tubing, a suction valve, and light source; and an access port or biopsy inlet, through which various devices and fluids can be passed into the working channel and out the distal end of the bronchoscope. The working head is attached to the insertion tube, which typically measures 580 mm in length and 6.3 mm in diameter. The insertion tube contains fiberoptic bundles, which terminate in the objective lens at the distal tip, light guides, and a working channel. Other endoscopes and bronchoscopes which may find use in embodiments of the present invention, or portions of which may find use with the present invention, are described in U.S. Pat. Nos. 7,473,219; 6,086,529; 4,586,491; 7,263,997; 7,233,820; and 6,174,307.

Such embodiments are not limited to a particular type or kind of steerable navigation catheter. In some embodiments, a steerable navigation catheter is configured to fit within the lumen of a primary catheter (e.g., endoscope) and a flexible sheath. In some embodiments, a steerable navigation catheter is of sufficient length to extend from an insertion site (e.g. mouth, incision into body of subject, etc.) to a treatment site (e.g. 50 cm . . . 75 cm . . . 1 m . . . 1.5 m . . . 2 m . . . 5 m . . . 15 m). In some embodiments, a channel catheter is of sufficient length to extend beyond the reach of a primary catheter (e.g., endoscope) to reach a treatment site (e.g. peripheral lung tissue). In some embodiments, a steerable navigation catheter engages a flexible sheath such that movement of the steerable navigation catheter results in synchronous movement of the flexible sheath. In some embodiments, as a steerable navigation catheter is inserted along a path in a subject, the flexible sheath surrounding the steerable navigation catheter moves with it. In some embodiments, a flexible sheath is placed within a subject by a steerable navigation catheter. In some embodiments, a steerable navigation catheter can be disengaged from a flexible sheath. In some embodiments, disengagement of a steerable navigation catheter and flexible sheath allows movement of the steerable navigation catheter further along a pathway without movement of the flexible sheath. In some embodiments, disengagement of a steerable navigation catheter and flexible sheath allows retraction of the steerable navigation catheter through the flexible sheath without movement of the flexible sheath.

Such embodiments are not limited to a particular type or kind of energy delivery device (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties). Such energy delivery devices are not limited to emitting a particular kind of energy. In some embodiments, the energy delivery devices are capable of emitting radiofrequency energy. In some embodiments, the energy delivery devices are capable of emitting microwave energy. Such devices include any and all medical, veterinary, and research applications devices configured for energy emission, as well as devices used in agricultural settings, manufacturing settings, mechanical settings, or any other application where energy is to be delivered.

The systems for therapeutic endoscopic procedures of the present invention are not limited to particular uses. Indeed, such systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the systems are configured for any type of procedure wherein the flexible sheath described herein can find use. For example, the systems find use for open surgery, percutaneous, intravascular, intracardiac, intraluminal, endoscopic, laparoscopic, or surgical delivery of energy.

The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the systems including the flexible sheath described herein are configured for movement and positioning, with minimal damage to the tissue or organism, at any desired location, including but not limited to, the lungs, brain, neck, chest, abdomen, and pelvis. In some embodiments, the systems are configured for guided delivery, for example, by computerized tomography, ultrasound, magnetic resonance imaging, fluoroscopy, and the like. Indeed, in some embodiments, all inserted components of such a system are configured for movement along a narrow and circuitous path through a subject (e.g. through a branched structure, through the bronchial tree, etc.).

In certain embodiments, the present invention provides methods of treating a tissue region, comprising providing a tissue region and a system described herein (e.g., a primary catheter (e.g., an endoscope), a flexible sheath as described herein, and an energy delivery device (e.g., a microwave ablation catheter), and at least one of the following components: a processor, a power supply, a temperature monitor, an imager, a tuning system, a temperature reduction system, and/or a device placement system); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the lung, heart, liver, genitalia, stomach, lung, large intestine, small intestine, brain, neck, bone, kidney, muscle, tendon, blood vessel, prostate, bladder, and spinal cord.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A flexible sheath for use in endoscopic procedures, comprising an elongate tubular body; the elongate tubular body comprising
   a) an elongate tubular body proximal end having a proximal end opening and an elongate tubular body distal end having a distal end opening, and an elongate tubular main body region positioned between the elongate tubular body proximal end and the elongate tubular body distal end;
   b) an elongate tubular body interior portion and an elongate tubular body exterior portion, wherein the elongate tubular body interior portion extends from the elongate tubular body proximal end to the elongate tubular body distal end, wherein the elongate tubular body exterior portion extends from the elongate tubular body proximal end to the elongate tubular body distal end; and
   c) a flexible-rigid region positioned only in the elongate tubular body distal end, wherein the flexible-rigid region is positioned on a most exterior region of the elongate tubular body exterior portion of the elongate tubular body distal end;
   wherein the elongate tubular body interior portion comprises a hollow port extending into the proximal end opening, through the elongate tubular body proximal end, through the elongate tubular body distal end, and out the distal end opening, wherein the size of the hollow port is such that it can accommodate the passing of a properly sized tool into the hollow port, through the hollow port, and out the hollow port;
   wherein the diameter of the flexible sheath is less than 5 mm;
   wherein the flexible-rigid region is configured to selectively alternate between a flexible state and a rigid state;
   wherein if the flexible-rigid region is in a rigid state then the elongate tubular body distal end is stabilized in a desired position with respect to a tissue region in contact with the flexible-rigid region; and
   wherein if the flexible-rigid region is in a flexible state then the elongate tubular body distal end is not stabilized with respect to a tissue region in contact with the flexible-rigid region.

2. The flexible sheath of claim 1,
   wherein the elongate tubular body interior portion further comprises an elongate tubular body coolant intake channel, an elongate tubular body distal end contained region, and an elongate tubular body coolant outtake channel,
   wherein the elongate tubular body distal end contained region is positioned at the elongate tubular body distal end,
   wherein the elongate tubular body interior portion is configured to a) receive coolant into the elongate tubular body proximal end via the elongate tubular body coolant intake channel, b) circulate the received coolant through the elongate tubular body coolant intake channel to the elongate tubular body distal end contained region, and c) circulate the coolant from the elongate tubular body distal end contained region through the elongate tubular body outtake channel and out of the elongate tubular body proximal end, wherein the diameter of the elongate tubular body outtake channel is larger than the diameter of the elongate tubular body intake channel, or the diameter of the elongate tubular body outtake channel is smaller than the diameter of the elongate tubular body intake channel, or the diameter of the elongate tubular body outtake channel and the diameter of the elongate tubular body intake channel are identical, wherein the hollow port, elongate tubular body intake channel, and elongate tubular body outtake channel are positioned in a multiaxial manner, or the hollow port, elongate tubular body intake channel, and elongate tubular body outtake channel are concentrically positioned in a coaxial manner, wherein the coolant is selected from water, glycol, air, inert gasses, carbon dioxide, nitrogen, helium, sulfur hexafluoride, ionic solutions, dextrose in water, Ringer's lactate, organic chemical solutions, oils, liquid metals, freons, halomethanes, liquified propane, other haloalkanes, anhydrous ammonia, sulfur dioxide, and a coolant gas compressed at or near its critical point.

3. The flexible sheath of claim 2, wherein the one or more flexible-rigid regions comprise thermoplastic polymers that have an appropriate glass-transition temperature of 15-25 degrees Celsius.

4. The flexible sheath of claim 3, wherein the thermoplastic polymer comprises copolymers of lactic acid and caprolactone, wherein the thermoplastic polymer comprises a copolymer of L-lactide and caprolactone with an L-lactide to caprolactone monomer ratio of 70:30 or less.

5. The flexible sheath of claim 2, wherein the temperature of the flexible-rigid region is regulated through circulation of coolant into and out of the elongate tubular body containment region, wherein maintenance of a flexible-rigid region temperature at approximately −40 degrees Celsius results in a flexible state for the flexible-rigid region, wherein maintenance of a flexible-rigid region temperature at approximately −5 degrees Celsius results in a rigid state for the flexible-rigid region, wherein the temperature of the flexible-rigid region is regulated through circulation of coolant into and out of the elongate tubular body containment region via a Joule-Thompson effect, an endothermic chemical reaction, or an exothermic chemical reaction, wherein the elongate tubular body interior region further comprises a steerable pull ring configured to permit a user to steer the flexible sheath in any desired manner, wherein the flexible sheath is designed to be operational within a microwave field or microwave zone without sustaining microwave field or microwave zone related damage, wherein the flexible sheath is designed to be operational within a tissue region experiencing high temperatures without sustaining high temperature related damage.

6. The flexible sheath of claim 1, wherein the properly sized tool is selected from an obturator, ablation probe, energy delivery device, or biopsy tool, wherein the flexible sheath has sufficient flexibility to access a circuitous route through a subject, wherein the composition of the elongate tubular body is a polymer material, wherein the composition of the elongate tubular body is selected from a higher temperature rated polymer material, fluorinated ethylene propylene (FEP), a thermoplastic copolyester, and a fluoropolymer or perfluoroalkoxy alkane (PFA).

7. A system comprising a primary catheter, the flexible sheath described in claim 1, and an energy delivery device.

8. The system of claim 7, wherein the primary catheter is an endoscope.

9. The system of claim 7, wherein the energy delivery device is a microwave energy delivery device.

10. A method of treating a tissue region, comprising providing a system of claim 7, inserting the primary catheter into a tissue region, inserting the flexible sheath through the primary catheter to a desired tissue region to be treated, securing the flexible sheath at the desired tissue region to be treated via the flexible-rigid region, inserting the energy delivery device through the flexible sheath to the desired tissue region to be treated, and treating the tissue region to be treated with the energy delivery device.

11. The method of claim 10, wherein the tissue region to be treated is within a subject.

12. The method of claim 11, wherein the subject is a human subject.

13. The flexible sheath of claim 1, wherein the temperature of the flexible-rigid region is regulated through circulation of a gas coolant into and out of the elongate tubular body containment region via a Joule-Thompson effect.

* * * * *